US011045550B2

(12) United States Patent
Lubda et al.

(10) Patent No.: US 11,045,550 B2
(45) Date of Patent: Jun. 29, 2021

(54) USE OF AN AMINO SUGAR AS PLASTICIZER

(71) Applicant: Merck Patent GmbH, Darmstadt (DE)

(72) Inventors: Dieter Lubda, Bensheim (DE);
Mengyao Zheng, Darmstadt (DE);
Alessandro Elia, Darmstadt (DE);
Nicole Di Gallo, Bensheim (DE);
Anja-Nadine Knuettel, Mannheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/301,185

(22) PCT Filed: May 10, 2017

(86) PCT No.: PCT/EP2017/061127
§ 371 (c)(1),
(2) Date: Nov. 13, 2018

(87) PCT Pub. No.: WO2017/194577
PCT Pub. Date: Nov. 16, 2017

(65) Prior Publication Data
US 2019/0134200 A1 May 9, 2019

(30) Foreign Application Priority Data

May 13, 2016 (EP) .................................. 16169691

(51) Int. Cl.
| | | |
|---|---|---|
| *A61K 47/26* | (2006.01) | |
| *A61K 9/14* | (2006.01) | |
| *A61K 31/496* | (2006.01) | |
| *A61K 31/192* | (2006.01) | |
| *A61K 31/4184* | (2006.01) | |
| *B29C 48/00* | (2019.01) | |
| *A61K 47/32* | (2006.01) | |
| *C08J 3/12* | (2006.01) | |
| *C08K 5/00* | (2006.01) | |
| *C08K 5/17* | (2006.01) | |
| *C08L 29/04* | (2006.01) | |
| *B29K 29/00* | (2006.01) | |

(52) U.S. Cl.
CPC .............. *A61K 47/26* (2013.01); *A61K 9/145* (2013.01); *A61K 9/146* (2013.01); *A61K 31/192* (2013.01); *A61K 31/4184* (2013.01); *A61K 31/496* (2013.01); *A61K 47/32* (2013.01); *B29C 48/022* (2019.02); *C08J 3/12* (2013.01); *C08K 5/005* (2013.01); *C08K 5/0016* (2013.01); *C08K 5/17* (2013.01); *C08L 29/04* (2013.01); *B29K 2029/04* (2013.01); *C08J 2329/04* (2013.01)

(58) Field of Classification Search
None
See application file for complete search history.

(56) References Cited

U.S. PATENT DOCUMENTS

| 5,456,923 A | 10/1995 | Nakamichi |
|---|---|---|
| 2013/0259920 A1 | 10/2013 | Crowley et al. |
| 2018/0028451 A1 | 2/2018 | Behrend |

FOREIGN PATENT DOCUMENTS

| CN | 103142501 A | 6/2013 |
|---|---|---|
| CN | 105456201 A | 4/2016 |
| EP | 2105130 A1 | 9/2009 |
| GB | 2409204 A | 6/2005 |
| JP | 2009531452 A | 9/2009 |
| JP | 05871294 B1 | 3/2016 |
| WO | 2011/140446 A2 | 11/2011 |

OTHER PUBLICATIONS

Crowley et al., "Pharmaceutical Applications of Hot-Melt Extrusion: Part I", Drug Development and Industrial Pharmacy, vol. 33, pp. 909-926, 2007.*
Repka et al., "Pharmaceutical Applications of Hot-Melt Extrusion: Part II", Drug Development and Industrial Pharmacy, vol. 33, pp. 1043-1057, 2007.*
International Search Report PCT/EP2017/061127 dated Sep. 8, 2017. (pp. 1-4).
Schilling S. U. et al.: "Citric acid as a solid-state plasticizer for Eudragit RS PO", J. Pharm. Pharmacol., vol. 59, No. 11, 2007, pp. 1493-1500.
Breitenbach J.: "Melt extrusion: from process to drug delivery technology", Eur. J. Pharm Biopharm., vol. 54, 2002, pp. 107-117.
Piyush Gupta et al: "Molecular interactions in celecoxib-PVP-meglumine amorphous system", vol. 57, No. 3, Mar. 1, 2005 (Mar. 1, 2005), pp. 303-310, XP002706382, ISSN: 0022-3573, Retrieved from the Internet [retrieved on Feb. 18, 2010].
K Crowley et al: "Hot Melt Extrusion of Amorphous Solid Dispersions", Pharmaceutical Sciences Encyclopedia: Drug Discovery, Development, and Manufacturing, 2015, XP002773166.
Abu-Diak et al. "An Investigation into the Dissolution Properties of Celecoxib Melt Extrudates: Understanding the Role of Polymer Type and Concentration in Stabilizing Supersaturated Drug Concentrations" Mol. Pharmaceutics 2011; vol. 8, No. 4, 1362-1371.
De Jaeghere et al:"Hot-melt extrusion of polyvinyl alcohol . . ." Int Journal of Pharmaceutics_ vol. 492, No. 1-2, 2015, pp. 1-9
Notice of Reasons for Refusal in corresponding JP2018559849 dated Mar. 8, 2021 (pp. 1-5).

* cited by examiner

Primary Examiner — Robert A Wax
Assistant Examiner — Randeep Singh
(74) Attorney, Agent, or Firm — Millen, White, Zelano and Branigan, P.C.

(57) ABSTRACT

The present invention relates to the use of an amino sugar as plasticizer in formulations comprising a polymer as carrier for active ingredients, in particular for compositions which are intensively mixed by treatment in a melt extrusion and then formulated by suitable post-treatment.

7 Claims, 9 Drawing Sheets

USE OF AN AMINO SUGAR AS PLASTICIZER

The present invention relates to the use of an amino sugar as plasticizer in formulations comprising a polymer as carrier for active ingredients, in particular for compositions which are intensively mixed by treatment in a melt extrusion and then formulated by suitable post-treatment.

BACKGROUND OF THE INVENTION

Nowadays the improvement of drug solubility and dissolution rate is an important issue, especially for biopharmaceutics classification system (BCS) Class II compounds. A variety of approaches have been used to enhance the solubility and dissolution rate of poorly water-soluble drugs, such as solid dispersion (SD), salt formation, solubilization, and particle size reduction. As such, solid dispersions can be created by a number of methods, including, but not limited to, spray-drying, melt extrusion, and thermokinetic compounding.

The SD method is one of the most commonly used pharmaceutical approaches to enhance the oral bioavailability of drugs with low aqueous solubility. The traditional method using organic solvent has been widely investigated, but this method has a potential problem of residual organic solvent.

The hot-melt extrusion (HME) technique has been developed to prepare SDs over the past two decades. HME is one of the most widely used processing techniques in the plastics industry. Building on knowledge from the plastics industry, formulators can extrude combinations of drugs, polymers and plasticizers into various final forms to achieve the desired drug-release profiles. HME offers some distinct advantages over other traditional methods. For example, it is solvent free, involves continuous dry processing and necessitates fewer processing steps, provides continuous operation, and scale-up capabilities, offers better content uniformity and can greatly improve bioavailability due to a higher degree of dispersion.

The active is mixed with other ingredients in a dry state. The hot melt extrusion mixtures of active ingredients, thermoplastic excipients, and other functional processing aids are filled in a hopper or feeder, conveyed, mixed, heated and softened or melted inside of an extruder.

The extrusion process subjects the materials to a heating process under intense mixing and the materials are extruded through nozzles to obtain the extrudates, which can be milled or micronized to obtain granules or particles, which are then incorporated into a suitable dosage form. Twin screw extruders are one of the most popular extruders and provide advantages such as short transit time, convenient material feed, high shear kneading, and less over-heating.

In this extrusion process, a thermoplastic carrier may be mixed with a pharmaceutical active substance and optional inert excipients and further additives. The mixture is fed into rotating screws that convey the powder into a heated zone where shear forces are imparted into the mixture until a molten mass is achieved.

For an amorphous dispersion via melt extrusion, the polymeric carrier vehicle must first possess a thermoplasticity that allows the polymer to be passed through the extruder, and on the other hand the carrier must be thermally stable at barrel temperatures above the glass transition temperature or melting point of the polymer.

As indicated above, during hot melt extrusion the active ingredients are mixed with and embedded in excipients, such as polymers and plasticizers. Furthermore, drug substances are exposed to elevated temperatures for a period of time. Although a variety of factors can affect the residence time distribution of an extruded substance, these times typically fall within the 1- to 2-min range (Breitenbach J., Melt extrusion: from process to drug delivery technology. Eur. J. Pharm Biopharm. (2002), 54, 107-117).

A prolonged exposure to elevated temperatures can induce decomposition of thermally labile compounds or accelerate decomposition of chemically unstable compounds. But the addition of processing aids, such as plasticizers, may allow processing to be carried out at a lower temperature (Schilling S. U. et al.; Citric acid as a solid-state plasticizer for Eudragit RS PO; J. Pharm. Pharmacol., (2007), 59(11), 1493-1500).

Therefore, as carriers for the application of (hot) melt extrusion, the polymers should have suitable properties such us: thermoplasticity, suitable glass transition temperature or melting point, thermostability at required processing temperature, no unexpected chemical interaction with active ingredients etc.

In this context, polyvinyl alcohol (PVA) is an excellent compound, which is suitable for (hot) melt extrusion, as carrier for pharmaceutically active ingredients.

Polyvinyl alcohol (PVA) is a synthetic water-soluble polymer that possesses excellent film-forming, adhesive, and emulsifying properties. It is prepared from polyvinyl acetate, where the functional acetate groups are either partially or completely hydrolyzed of the resulting esterified polymer forming functional alcohol groups.

Chemical and physical properties of PVA, such as viscosity, solubility, thermal properties, etc., are very depending on its degree of polymerization (chain length of PVA polymer) and hydrolysis.

As the degree of hydrolysis increases, the solubility of the polymer in aqueous media increases, but also the crystallinity of the polymer increases. In addition to this, the glass transition temperature varies depending on its degree of hydrolysis. For example, a 38% hydrolyzed material has no melting point, but a glass transition temperature of approximately 48° C., whereas a 75%-88% hydrolyzed material has a melting temperature of approximately 190-200° C.

Polyvinyl alcohol is soluble in water, but almost insoluble in almost all organic solvents, excluding, in some cases, in ethanol. This aspect of the polymer makes it very difficult to form amorphous and solid dispersions through spray drying when the drug has also a limited solubility in aqueous media.

U.S. Pat. No. 5,456,923 A provides a process for producing a solid dispersion, which overcomes disadvantages of the conventional production technology for solid dispersions. The process comprises employing a twin-screw extruder in the production of a solid dispersion. In accordance with this, a solid dispersion can be expediently produced without heating a drug and a polymer up to or beyond their melting points and without using an organic solvent for dissolving both components and the resulting solid dispersion has excellent performance characteristics. The process claims a polymer that is natural or synthetic and can be employed as a raw material where the polymer's functions are not adversely affected by passage through the twin screw extruder.

EP 2 105 130 A1 describes a pharmaceutical formulation comprising a solid dispersion having an active substance embedded in a polymer in amorphous form, and an external polymer as a recrystallization inhibitor independently of the solid dispersion. The external polymer is claimed as a solution stabilizer. The active substance should be sparingly soluble or less sparingly soluble in water. Thermoplastic polymers are claimed as drug carriers to form a solid dispersion. It is claimed that the solid dispersion is obtained by melt extrusion. The process comprises melting and mixing the polymer and the active ingredient, cooling, grinding, mixing with the external polymer, and producing a pharmaceutical formulation. It is claimed that the melting is carried out at a temperature below the melting point of the drug. It is also claimed that the melting is carried out at a temperature above the $T_9$ or melting point of the polymer, but from 0.1-5° C. below the melting point of the API. The melting point of pharmaceutical grades of PVA is normally above 178° C., although the glass transition temperature is in the range of 40-45° C.

As such, polyvinyl alcohol (PVA) can be applied in various routes of administration to treat a variety of medical conditions and it is used in a wide range of pharmaceutical dosage forms, including ophthalmic, transdermal, topical and especially oral applications.

But in order to manufacture a specific dosage formulation of an active ingredient in form of a solid dispersion in a polymer matrix consisting of PVA, the active ingredient should be embedded homogeneously distributed in the polymer matrix. It is desirable to achieve this by hot melt extrusion.

The requirements for thermoplastic polymers useful as HME excipients are: pharmaceutical grade, suitable glass transition temperature, high thermal stability, no toxicity and high biocompatibility. Since it has been found that essential requirements are met in this respect by PVA, it can be chosen under certain conditions in pharmaceutical formulations as carriers for active compounds contained. Now, PVA is a well known polymer with varying degrees of hydroxylation melting points, but which are too high for a hot melt extrusion process with active ingredients.

PROBLEM TO BE SOLVED

For preparation of pharmaceutical formulations in form of solid dispersions it is a common method to homogenize the required ingredients with each other by hot melt extrusion. But because of the already above-described problematic chemical and physical properties of polyvinyl alcohol (PVA), it is difficult to produce corresponding solid compositions comprising PVA as carrier for active ingredients by hot melt extrusion without affecting the active ingredient at the required temperatures and optionally its partial decomposition.

Therefore, it is an object of the present invention to provide a suitable additive, by which the melting point of the entire mixture with a pharmaceutical active ingredient and PVA as a carrier can be lowered to a temperature, which is below the melting point $T_m$ of the applied PVA and which is as low that the active ingredient remains stable during melt extrusion. It is a further object of the present invention to provide a suitable additive, by which the viscosity of the mixture comprising PVA as carrier or excipient for the active ingredient during the extrusion process. It is also an object of the present invention to provide an additive by which the viscosity of said mixture is adjusted during extrusion in a suitable manner.

Therefore, it is also an object of the present invention to provide a formulation comprising PVA as carrier for an active ingredient and at least an additive in suitable amounts, which shows a melting point $T_m$ below the melting point of the applied PVA and which has a suitable viscosity, such that the comprising active ingredient remains stable during hot melt extrusion and that an extrusion is made possible without any interruption.

Particularly, it is therefore an object of the present invention to provide a composition comprising PVA and an additive, and optionally other ingredients, which allows the formulation of stable homogeneous mixtures in form of solid dispersions containing active ingredients (APIs) and which are processed by hot melt extrusion.

SUMMARY OF THE INVENTION

Unexpectedly it was found by experiments that for the preparation of pharmaceutical formulations the use of low molecular weight amino polyol as plasticizer in polymer containing compositions for hot melt extrusion (HME) or melt extrusion processes is associated with great advantages. Suitable amino polyols are selected from the group D-glucosamine, D-galactosam nine, mannosamine, D-fucosamine, N-acetyl-D-fucosamine, N-acetyl-D-glucosamine, N-acetyllactosamine, N-acetylmannosamine, meglumine (D-(−)-N-methylglucamine) and sialic acid. A particularly suitable amino polyol for this application is meglumine (D-(−)-N-methylglucamine). The use of these amino polyols for the preparation of pharmaceutical formulations containing polymer as carrier matrix is characterized in that the applied amino polyol reduces the glass transition temperature $T_9$ and the melting temperature $T_m$ of said polymer containing compositions in hot melt extrusion (HME) or melt extrusion processes. Advantageously the applied amino polyol additionally reduces the melting viscosity of the polymer containing thermoplastic composition.

A further advantageous effect is that the use of amino polyol, especially of meglumine stabilizes thermal instable active pharmaceutical ingredients (APIs) and reduces their thermal degradation and acts as solubilisation-enhancer for the applied poorly water-soluble API during hot melt extrusion (HME) or melt extrusion and as stabilizer for the produced amorphous solid dispersion of the API in the polymer matrix during hot melt extrusion (HME) or melt extrusion. This solubilisation enhancing effect is especially advantageous if acidic APIs are used for the production of the compositions according to the invention. Particularly preferred in this context is the use of an amino polyol in polyvinyl alcohol (PVA) containing compositions for hot melt extrusion (HME) or melt extrusion processes.

Furthermore, the use of these amino polyols is particularly advantageous for the preparation of compositions wherein a) the amino polyol is contained in a weight percentage amount in the range of 5-40%, b) the polymer is contained in a weight percentage amount in the range of 60-95% and c) the API is contained in a weight percentage amount in the range of 0.01-40%, with the proviso that the sum of all ingredients of the composition add up to 100%.

Thus, part of the present invention is also a powdery composition, comprising at least one thermoplastic polymer, and at least one amino sugar, selected from the group D-glucosamine, D-galactosamnine, mannosamine, D-fucosamine, N-acetyl-D-fucosamine, N-acetyl-D-glucosamine, N-acetyllactosamine, N-acetylmannosamine, meglumine (D-(−)-N-methylglucamine) and sialic acid as plasticizer, at least one active pharmaceutical ingredient and optionally one or more additives, selected from the group surface active material, anti-oxidant, stabilizing agent, solubility-enhancing agents, pH control agents and flow regulators, which is obtained by the steps of
a. physical blending or granulating of the ingredients into a homogeneous mixture,
b. hot melt extrusion or melt extrusion and
c. subsequent confectioning into a powder.

In particular, part of the invention are such powdery compositions comprising polyvinyl alcohol as thermoplastic polymer in combination with meglumine as plasticizer and at least one active pharmaceutical ingredient. A particular advantage of this powdery composition is that it is a long-term stable amorphous solid dispersion of at least one active pharmaceutical ingredient in a carrier matrix of a thermoplastic polymer and of at least one amino sugar.

The present invention also provides a process for the production of the above powdery compositions according to the invention, characterized in that
a) at least one thermoplastic polymer, at least one amino sugar, at least one active pharmaceutical ingredient and optionally one or more additives, selected from the group surface active material, anti-oxidant, stabilizing agent, solubility-enhancing agents, pH control agents and flow regulators, are processed into a homogeneous mixture by physical blending or granulating, and
b) hot melt extrusion or melt extrusion of this homogeneous mixture is processed, whereby a solid dispersion of the API in the carrier matrix of a thermoplastic polymer and of at least one amino sugar is built and
c) that the extrusion product is subsequently confectioned into a powder.

This process is characterized in that polyvinyl alcohol, meglumine and at least one active pharmaceutical ingredient and optionally one or more additives, selected from the group surface active material, anti-oxidant, stabilizing agent, solubility-enhancing agents, pH control agents and flow regulators, are processed into a homogeneous mixture by physical blending or granulating, which is then processed by hot melt extrusion or melt extrusion at a temperature 5 150° C. and confectioned into a powder.

DETAILED DESCRIPTION OF THE INVENTION

Over the last years, hot melt extrusion (HME) has been introduced as pharmaceutical manufacturing technology and has now become a well-known processing with benefits like continuous and effective process, limited number of processing steps, solvent free etc. During hot melt extrusion, a mixture of active ingredient(s) and thermoplastic excipients, and other functional processing aids, is heated and softened or melted inside the extruder and extruded through a nozzle into different forms.

In order to manufacture a specific hot melt extrusion dosage form, the active ingredients are embedded in a polymer matrix. The requirements for a thermoplastic polymer, which is intended to be used as HME excipient, are as follows:
1. The polymer must have a suitable pharmaceutical grade.
2. Its glass transition temperature must have an appropriate low level.
3. The polymer must show high thermal stability and it must be mechanically stable with respect to shear forces.
4. It must not be toxic must have a high biocompatibility.

In this context, polyvinyl alcohol appears to be a suitable polymer. It is commercially available in various hydroxylation grades and in various pharmaceutical qualities.

In this regard, pharmaceutical grade polyvinyl alcohols appear to be a good choice for the preparation of formulations comprising active ingredients, which are processed by HME.

PVA is a synthetic, water-soluble polymer that possesses excellent film-forming, adhesive, and emulsifying properties. It is prepared by the polymerization of vinyl acetate and functional acetate groups are either partially or completely hydrolyzed to alcohol functional groups. Chemical and physical properties of PVA, such as viscosity, solubility, thermal properties etc. depend on its degree of polymerization (chain length of PVA polymer) and the degree of hydrolysis. As the degree of hydrolysis increases, the solubility of the polymer in aqueous media increases, but also crystallinity and melting temperature of the polymer increase. In addition to this, the glass transition temperature varies depending on its degree of hydrolysis. For example, a 38% hydrolyzed material has no melting point, but a glass transition temperature of approximately 48° C., whereas a 75% hydrolyzed material has a melting temperature of approximately 178° C., an 88% hydrolyzed material has a melting point of approximately 196° C., and a 99% material has a melting point of approximately 220° C., but the polymer tends to degrade rapidly above a temperature of 200° C.

Polyvinyl alcohol is soluble in water, but almost insoluble in almost all organic solvents, excluding, in some cases, like in ethanol. This aspect makes it very difficult to form amorphous and solid dispersions by spray drying.

Nevertheless, polyvinyl alcohol (PVA) is known as a carrier in a variety of different routes of pharmaceutical administrations and for the treatment of a variety of medical conditions, and it is used in a wide range of pharmaceutical dosage forms, including ophthalmic, transdermal, topical, and in particular as formulations for oral applications.

The United States Pharmacopeia-National Formulary mandates that an acceptable polyvinyl alcohol for use in pharmaceutical dosage forms must have a percentage of hydrolysis between 85 and 89%, as well as a degree of polymerization between 500 and 5000. The degree of polymerization (DM) is calculated by the equation:

$$DM = (\text{Molar Mass})/((86)-(0.42(\text{the degree of hydrolysis})))$$

The European Pharmacopoeia mandates that an acceptable polyvinyl alcohol for use in pharmaceutical dosage forms must have an ester value no greater than 280 and a mean relative molecular mass between 20,000 and 150,000. The percentage of hydrolysis (H) can be calculated from the following equation:

$$H = ((100-(0.1535)(EV))/(100-(0.0749)(EV))) \times 100$$

Where EV is the ester value of the polymer. Thus, only polymers with a percentage of hydrolysis greater than 72.2% are acceptable according to the European Pharmacopoeia monograph.

For PVAs it is well known that its high melting points are too high to be extruded as such together with active ingredients, which possess lower melting point than the applied PVA grade.

This means, that an agent has to be found, whereby the melting point $T_m$ can be lowered. At the same time it would be advantageous if the viscosity of the PVA containing mixture is reduced during extrusion by the same additive.

By adding this additive to the mixture comprising PVA as a carrier for the pharmaceutical active ingredient, it is aimed to obtain a formulation that will form a stable, solid and amorphous mixture with the active substance after a treatment by hot-melt extrusion.

Generally, it is known to add plasticizers, plasticizing agents or lubricants for improvement of flowability of pharmaceutical formulations, if the latter can poorly be compressed into tablets. These additives are mixed intensively with all compounds of the tablet formulation before tableting, so that a homogeneous mixture of the ingredients is obtained. Subsequently, this mixture is supplied to tableting, whereby the mixture is compressed under the influence of pressure to form tablets.

Now, surprisingly it has been found by experiments that the addition of at least a further excipient in blends with polyvinyl alcohol may lead to a melting point of the mixture which is significantly reduced. At the same time, melts of these mixtures also exhibit significantly reduced viscosities.

In particular, meglumine has excellent properties in this context. Meglumine, or D-(−)-N-Methylglucamine, is an amino sugar derived from sorbitol showing a pKa value of 9.60. It is a commonly used additive and it is an acceptable pharmaceutical excipient, which is FDA approved. It is used in contrast media and it can be applied in different administration routes. As a functional excipient it is well known as stabilizer for active pharmaceutical ingredients and as solubilizer in pharmaceutical formulations. Meglumine is commercially available from Merck Millipore in high purity and pharmaceutical grade.

Meglumine is an amino sugar derived from sorbitol, which can be used as plasticizer. Meglumine and sorbitol show similar physical properties, like low glass transition temperatures and melting points, low melt viscosities, high thermo-stabilities, good water solubilities etc.

The experiments carried out have shown that meglumine is not only suitable as an excipient for pharmaceutical active ingredients, but it is also useful as novel plasticizer or lubricant that be used in formulations for melt extrusion.

Surprisingly, it has been found by the analytical data of the experiments with compositions of PVA comprising meglumine, that meglumine is effective as plasticizer and can be used to reduce the melting point and the melt viscosity of mixtures containing PVA as excipient. It was also found, that temperature-sensitive pharmaceutical active ingredients can be effectively and gently extruded through addition of meglumine at a lower temperature. Furthermore, it was found by the investigations that meglumine has a stabilizing effect on active pharmaceutical ingredients, in particular, it has a stabilizing effect on amorphous solid dispersions with high drug concentration.

Figure 1:
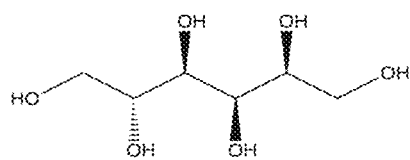
FIG. 1: structure of sorbitol
Figure 2:
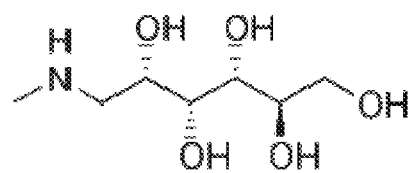
FIG. 2: structure of meglumine

Generally, substances should meet different essential requirements, if it is planned to use them for the production of pharmaceutically active compositions as envisaged above. From literature it is known, that poorly soluble active pharmaceutical ingredients can be formulated together with suitable carriers and other additives by HME into compositions providing improved bioavailability of the active ingredient.

Our experiments have now shown that compositions of poorly soluble active agents together with PVA as a carrier matrix in combination with meglumine can be processed by HME into amorphous solid dispersions that have the desired beneficial properties.

The materials used in the production of hot-melt extruded dosage forms must meet the same level of purity and safety as those used in traditional dosage forms. Most of the compounds used in production of hot-melt extruded pharmaceuticals have already been used in production of other solid dosage forms such as tablets, pellets, and transdermals.

An essential condition for hot melt extrudability of a polymer composition is a suitable low melting temperature, $T_m$, which is combined with low melt viscosity of the mixture during the extrusion process. In order to reduce the melting temperature, but also the melt viscosity often plasticizers are needed to facilitate the hot melt extrusion process and to improve the physical and mechanic properties of final products. Plasticizers can reduce the glass transition temperature, $T_g$, by increasing the free volume between polymer chains and of their mobility.

The materials applied for the production of the pharmaceutical composition by hot melt extrusion must possess some degree of thermal stability in addition to acceptable physical and chemical stability. Thermal stability of all individual compounds is a prerequisite for the process and should be sufficient to withstand the production process. Not only the polymer must be stable at the processing temperature but especially the comprising active pharmaceutical ingredient (API), in particular thermo-sensitive or thermo-instable APIs need to be protected against decomposition during hot melt extrusion. Here, in the present invention, the combination of PVA with meglumine as additional carrier exerts a synergistic effect together with PVA during hot melt extrusion and thus stabilizing of the active ingredient. This stabilizing effect of the applied API is combined with a lowering of the melting point of the entire mixture.

Now, our experiments have shown, that compositions comprising polyvinyl alcohol as carrier matrix in combination with meglumine can be processed by hot melt extrusion at a much lower temperature than one would expect based on the melting temperature of the polymer contained.

Advantageously, the extrusion can be carried out at a temperature of less than or equal to 150° C., and, under suitable conditions, the temperature in the extruder can be set even lower than 140° C.

As mentioned earlier, hot-melt extrusion can enhance drug solubility by stabilizing drugs in amorphous form in the polymer matrix and by de-aggregating drug particles in the applied carrier. A further effect of this manufacturing process by melt extrusion is an improved wettability of drugs and the results of our own experiments have shown, that poorly water-soluble drugs and a hydrophilic polymer, like PVA, can be processed to a solid dispersion by HME. In this context, a substantially improvement of bioavailability and solubility of the drug was found by the inventive combination of PVA with meglumine as further carrier.

The prerequisite for a long-term stable formulation of an active ingredient is a solid amorphous dispersion in a carrier. Dosage forms obtained by melt-extrusion usually have good long-term stability. But still the physical and chemical stability of the extruded product depends on the nature of the API, the comprising polymers, excipients, further ingredients and the physical state of the API in the final dosage form, but also on storage and packing conditions.

Advantageously, a positive influence of the inventive combination of PVA with meglumine as further carrier and the HME processing can also be seen in this context.

The mixture of HME excipients including polymer, preferably PVA, and plasticizer and ingredients should be fed into the feeder of the extruder, melted and extruded to build a stable amorphous solid dispersion of the applied API.

As used herein, the term "plasticizer" includes all compounds capable of plasticizing the applied polymer, preferably polyvinyl alcohol as characterized above. The plasticizer should be able to lower the glass transition temperature or softening point of the polymer in order to allow for lower processing temperature, extruder torque and pressure during the hot-melt extrusion process. Plasticizers generally broaden the average molecular weight of the polymer thereby lowering its glass transition temperature or softening point. Plasticizers also generally reduce the viscosity of a polymer melt thereby allowing for lower processing temperature and extruder torque during hot-melt extrusion. It is possible that the plasticizer will impart some particularly advantageous physical properties to the produced pharmaceutical formulation.

As used herein, the term polyvinyl alcohol is intended to characterize polyvinyl alcohol grades, which are hot melt extrudable or melt extrudable and are those polymers having viscosities≤40 mPa·s, whereby the viscosity being measured on 4% aqueous solution at 20° C. (DIN 53015). These particular polyvinyl grades fulfilling said conditions are preferably selected preferably from the group: PVA 3-80, PVA 3-85, PVA 3-88, PVA 3-98, PVA 4-88, PVA 4-98, PVA 5-74, PVA 5-82, PVA 6-88, PVA 6-98, P VA 8-88, PVA 10-98, PVAPVA 13-88, PVA 15-99, PVA 18-88, PVA 20-98, PVA23-88, PVA 26-80, PVA 26-88, PVA28-99, PVA 30-98, PVA 30-92, PVA 32-88, PVA 40-88, most preferred from the group: PVA 3-88, PVA 4-88, PVA 5-74, PVA 5-88, PVA 8-88, and PVA 18-88.

It is found by experiments that including an amino polyol as plasticizer in the present formulation will alter its release profile. Generally, increasing the amount of plasticizer present will increase the release rate of the therapeutic compound.

It is contemplated and within the scope of the invention, that amino polyol, preferably meglumine, can be used in combination with at least another plasticizer in the present formulation.

The plasticizer employed herein may be a solvent for the polymer, especially for the polyvinyl alcohol, at the temperature where the formulation is prepared. Such plasticizer, when mixed with the polymer above a characteristic temperature at which the polyvinyl alcohol becomes soluble therein, may dissolve the polyvinyl alcohol. Upon cooling, the mixture forms an amorphous dispersion of the comprising active ingredient in the polymer matrix.

Plasticizers useful in the invention include, by way of example and without limitation, low molecular weight amino alcohols.

Such plasticizers may be amino sugars, selected from the group D-glucosamine, D-galactosamnine, mannosamine, D-fucosamine, N-acetyl-D-fucosamine, N-acetyl-D-glucosamine, N-acetyllactosamine, N-acetylmannosamine, meglumine (D-(−)-N-methylglucamine) and sialic acid. Preferably meglumine (D-(−)-N-methylglucamine) is employed as plasticizer for polyvinyl alcohol.

The amount of plasticizer used in the formulation will depend upon its composition, physical properties, effect upon the polymer, its interaction with other components of the formulation, ability to solubilize the therapeutic compound or other factors to be considered in the preparation of pharmaceutical formulations. The amount of plasticizer present in the formulation affects its properties. By way of example, when the plasticizer is meglumine, its content will generally not exceed 30% wt. of the formulation.

Pharmaceutical Formulations

As used herein, the term "active pharmaceutical ingredient" or "API" means an organic chemical substance having desired beneficial and therapeutic effects in mammals. Such compounds are generally classified as pharmaceuticals or biologicals. As long as the therapeutic compound can diffuse from the formulation when exposed to a biological fluid, its structure is not especially critical.

The APIs contemplated within the scope of the invention include hydrophobic, hydrophilic and amphiphilic compounds. They may be in their free acid, free base, or pharmaceutically acceptable salt forms. They may be derivatives or prodrugs of a given pharmaceutical.

It will be appreciated that certain APIs used in the present invention may contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and geometric trans-isomers of the therapeutic compounds are described and may be isolated as a mixture of isomers or as separated isomeric forms. All chiral, diastereomeric, racemic forms and all geometric isomeric forms of a structure are intended, unless the specific stereochemistry or isomer form is specifically indicated.

It is not necessary for the API to be soluble in any given formulation component. The API may be either dissolved, partially dissolved or suspended in the polymer matrix of the formulation. It is necessary for the API to be stable during the hot-melt extrusion process conditions used. By stable, it is meant that a significant portion of the therapeutic compound will not be significantly degraded or decomposed throughout the hot-melt extrusion process.

The APIs which may be hot-melt extruded in the formulation of the invention may be used for treating indications such as, by way of example and without limitation, inflammation, gout, hypercholesterolemia, microbial infection, AIDS, tuberculosis, fungal infection, amoebic infection, parasitic infection, cancer, tumor, organ rejection, diabetes, heart failure, arthritis, asthma, pain, congestion, urinary tract infections, vaginal infection, seizure related disorder, depression, psychosis, convulsion, diabetes, blood coagulation, hypertension and birth control.

Loading of the APIs into the final formulation may be accomplished following the techniques below. Generally, the therapeutic compound is loaded by premixing it with the polyvinyl alcohol and any other formulation components and hot-melt extruding the mixture. When solids are present in the mixture, they may be, by way of example and without limitation, either powdered, crystalline, amorphous, pelletized, beaded, spheronized, granular or the like.

It should be understood that the amount of API loaded into the formulation may be varied according to, for example, the polymer: API or the polymer: plasticizer: API ratios used in the pre-extruded mixture. Although a given loading method may be optimal for a particular polyvinyl alcohol: API combination, all of the described methods will generally result in API loading to some degree.

The therapeutic amount of API loaded into the formulation will vary according to the pharmacological activity of the API, the indication being treated, the targeted dosing regimen, the projected method of administration, the integrity or stability of the final formulation or other such reasons.

Hot-Melt Extrusion Process

As used herein, the term "hot-melt extrudable" refers to a compound or formulation that may be hot-melt extruded. A hot-melt extrudable polymer is one that is sufficiently rigid at standard ambient temperature and pressure but is capable of deformation or forming a semi-liquid state under elevated heat or pressure.

Although the process referred to above has been called a hot-melt extrusion, other equivalents processes may be used. By using any of these methods, the formulation may be shaped as needed according to the desired mode of administration, e.g. tablets, pills, lozenges, suppositories and the like.

The hot-melt extrusion process employed in some embodiments of the invention is conducted at an elevated temperature, i.e. the heating zone(s) of the extruder is above room temperature (about 20° C.). It is important to select an operating temperature range that will minimize the degradation or decomposition of the active pharmaceutical compound during processing. The operating temperature range is generally in the range of from about 60° C. to about 160° C. as determined by the following experiments and by the setting for the extruder heating zone(s). These experiments have shown, that the operating temperature can be set at temperatures 5 150° C.

In a preferred embodiment of the invention, the hot-melt extrusion can be conducted employing a solid, powdered or other such feed comprising polyvinyl alcohol, meglumine and an active ingredient and optionally further compounds. Dry feed is advantageously employed in the process of the present invention.

The hot-melt extrusion process is generally described as follows. An effective amount of a powdered API is mixed with a suitable polymer acting as carrier matrix, and as disclosed here, with a plasticizer such as meglumine. Other components may be added in the various embodiments of the invention.

In the inventive embodiments of the present invention, it has proven to be advantageous when
a) the amino polyol is contained in the composition in a weight percentage amount in the range of 5-40%,
b) the polymer is contained in a weight percentage amount in the range of 60-95% and
c) the API is contained in a weight percentage amount in the range of 0.01-40%,
with the proviso that the sum of all ingredients of the composition add up to 100%, depending on the desired release profile, the pharmacological activity and toxicity of the selected active pharmaceutical ingredient and other such considerations. The mixture is then placed in the extruder feeder and passed through the heated area of the extruder at a temperature which will melt or soften the polymer and plasticizer, to form a matrix throughout which the active ingredient is homogeneously dispersed. The molten or softened mixture then exits via a die, or other such element, at which time, the mixture (now called the extrudate) begins to harden. Since the extrudate is still warm or hot upon exiting the die, it may be easily shaped, molded, chopped, ground, molded, spheronized into beads, cut into strands, tableted or otherwise processed to the desired physical form. Preferably, the extrudate is confectioned to a powdery composition.

The extruder used to practice the invention may be any such commercially available model equipped to handle dry feed and having a solid conveying zone, one or multiple heating zones, and an extrusion die. A two stage single screw extruder is one such apparatus. It is particularly advantageous for the extruder to possess multiple separate temperature controllable heating zones.

Many conditions may be varied during the extrusion process to arrive at a particularly advantageous formulation. Such conditions include, by way of example, formulation composition, feed rate, operating temperature, extruder screw RPM, residence time, configuration, heating zone length and extruder torque and/or pressure. Methods for the optimization of such conditions are known to the skilled artisan.

EXAMPLES

Even without any further explanations, it is assumed that a person skilled in the art can make use of the above description in its widest scope. The preferred embodiments and examples are therefore to be regarded merely as descriptive but in no way limiting disclosures.

For better understanding and for illustration, examples are given below which are within the scope of protection of the present invention. These examples also serve for the illustration of possible variants.

The complete disclosure of all applications, patents and publications mentioned above and below are incorporated by reference in the present application and shall serve in cases of doubt for clarification.

It goes without saying that, both in the examples given and also in the remainder of the description, the quoted percentage data of the components present in the compositions always add up to a total of 100% and not more. Given temperatures are measured in ° C.

Methods and Materials
1. Materials:
Meglumine: 1-Desoxy-1-methylaminosorbit
Producer: Merck KGaA product
CAS-number: 6284-40-8
EC-number: 228-506-9
Quality: Ph Eur,JP,USP
2. Experiments and Methods
2.1 Equipment for Experiments
Extruder: Brabender® Mini-Compounder KETSE 12/36 D)
Physical blend of meglumine, other excipients and active ingredients: TURBULA® Shaker-Mixer Miller to grand the extrudate in powder: IKA®M 20 Universalmühle
Brabender® Pelletizer
3.1. Characterization Methods
3.1.1. Extrudability
At first, mixture of meglumine, polymer and active ingredient were blended using TURBULA® Shaker-Mixer homogeneously (the concentration of polymer and active ingredient depends on the types and physical properties of them). The mixture was then loaded into the extruder with well designed extrusion parameters, such as feeding rate, screw design, screw speed, extrusion temperature etc. The set up of those parameters depend also on the types and physical properties of polymer and active ingredients. As the boiling point temperature of meglumine is normally 210° C., the extrusion temperature should be controlled under 210° C.

3.1.2. Milling of Extrudate
The obtained extrudate can be micronized into fine particle (<1500 µm) using a miller or granulated as beads (1500-5000 µm) using a Brabender® Pelletizer.

Figure 3:
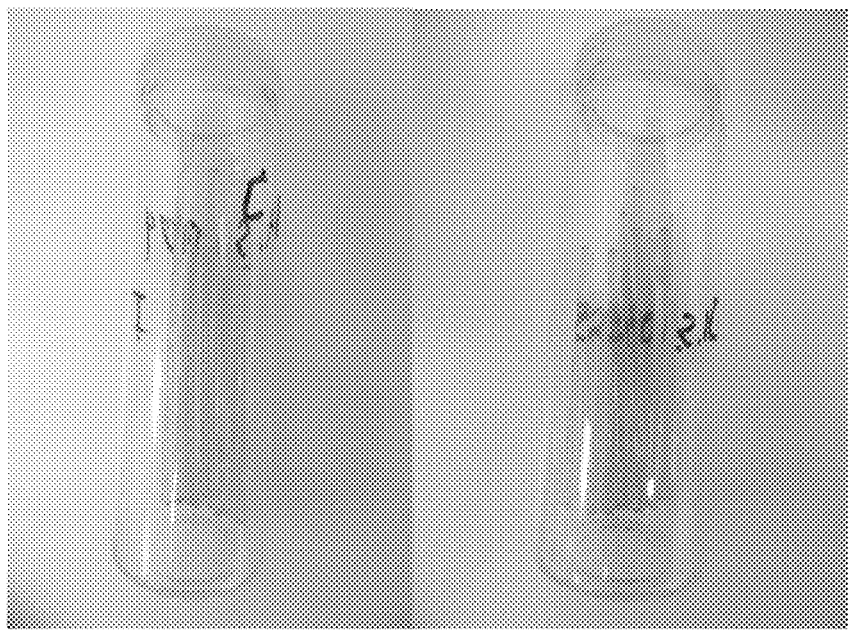
FIG. 3: Extrudate of polyvinyl alcohol and meglumine (75/25; left: extrudate processed 140° C.; right: extrudate processed at 160° C.

3.1.3. Dissolution
For the real time dissolution performance, we used following equipments:
System 1:
Sotax AT 7 on/offline
Pumpe CY-7-50
Fraction collector: C613 14 "Kanal 3 Wege Ventilbalken für Reagenzgläser"
Agilent 8453 Photometer
System 2
Sotax AT 7 on/offline
Pumpe CP 7-35
Fraction collector: C 613 14 "Kanal 3 Wege Ventilbalken für Vials"
Photometer Analytik Jena Specord 200 plus
4.1.1. Homogeneity with APIs
The concentration of the comprising active ingredient from different positions of extrudate was analyzed by NMR spectroscopy.
4.1.2 Results Based on Polyvinyl Alcohol as Thermoplastic Polymer for HME
4.1.2.1 Efficiency of Tg/Tm and Melt Viscosity Reduction
Meglumine can be used as plasticizer for thermoplastic polymer and changes the behavior of hot melt extrusion. Whereas an minimum extrusion temperature of 190° C.-200° C. (depends on PVA types) is necessary to process polymer poly vinyl alcohol, and only 140° C.-150° C. is necessary to process the mixture with addition of 25% meglumine.
FIG. 3: Extrudate of polyvinyl alcohol and meglumine (75/25; left: extrudate processed at 140° C.; right: extrudate processed at 160° C.

TABLE 1

HME temperature of mixture PVA/meglumine in different concentration:

| Composition | HME Temp. (minimum) [° C.] | Extrudate | Stability |
|---|---|---|---|
| PVA4-88/ Meglumine = 5/1 | 165 | — transparency | no recrystllisation |
| PVA4-88/ Meglumine = 4/1 | 160 | — transparency | no recrystllisation |
| PVA4-88/ Meglumine = 3/1 | 140-150 140 | — transparency | no recrystllisation no recrystllisation |
| PVA4-88/ Meglumine = 2/1 | 140 | — transparency | no recrystllisation |
| PVA4-88/ Meglumine = 1/1 | | — transparency | |
| PVA4-88/ Meglumine = 1/2 | Not extrudable, too liquid | — | — |

4.1.2.2. Dissolution and Solubility Improvement of Active Ingredients
To evaluate the performance of meglumine as plasticizer for polymer and stabilizing agent and solubility enhancing for acidic active ingredients, we chose model active ingredients with different pKa value:
1) Ibuprofen: pKa (strongest acidic)=3.8
2) Telmisartan: pKa (strongest acidic)=3.65
3) Itraconazole: pKa (strongest basic)=3.92
4) Naproxen: pKa (strongest basic)=4.19
The extrudate from API and poly vinyl alcohol, with and without meglumine were analyzed regarding dissolution, polymorphy and stability.

Example 1: Ibuprofen (Tm=78° C., Acidic Active Ingredient)

Figure 4:
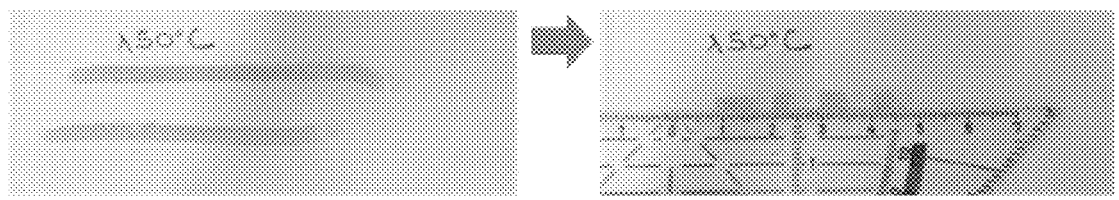
FIG. 4: Extrudate of 20% Ibuprofen with PVA/meglumine (75/25): 80° C./150° C./150° C./150° C./150° C.
Figure 5:
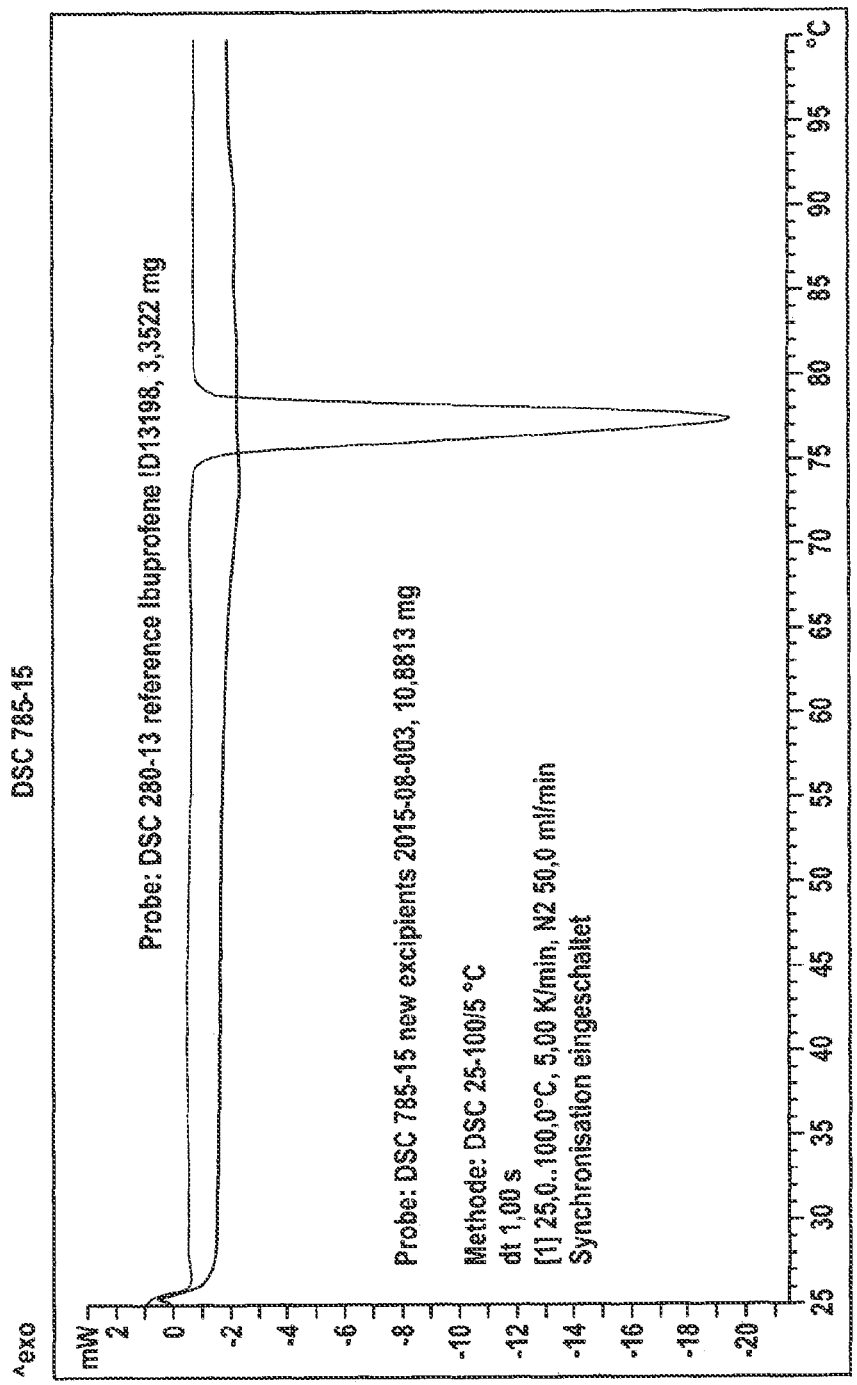
FIG. 5: DSC of an extruded composition comprising amorphous ibuprofen in a concentration of 20% w/w.
Figure 6:
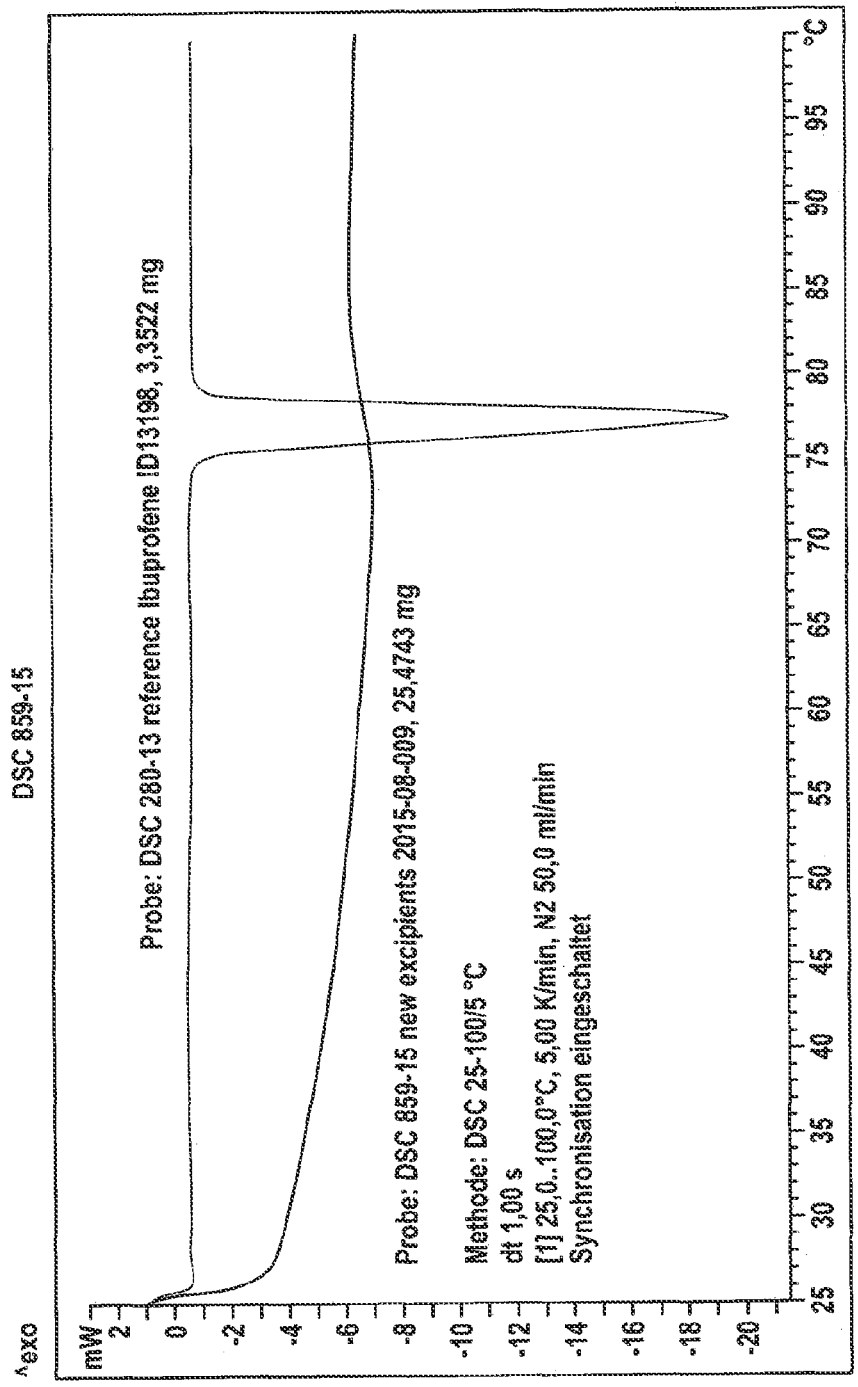
FIG. 6: DSC of an extruded composition comprising amorphous ibuprofen in a concentration of 30% w/w.
Figure 7:
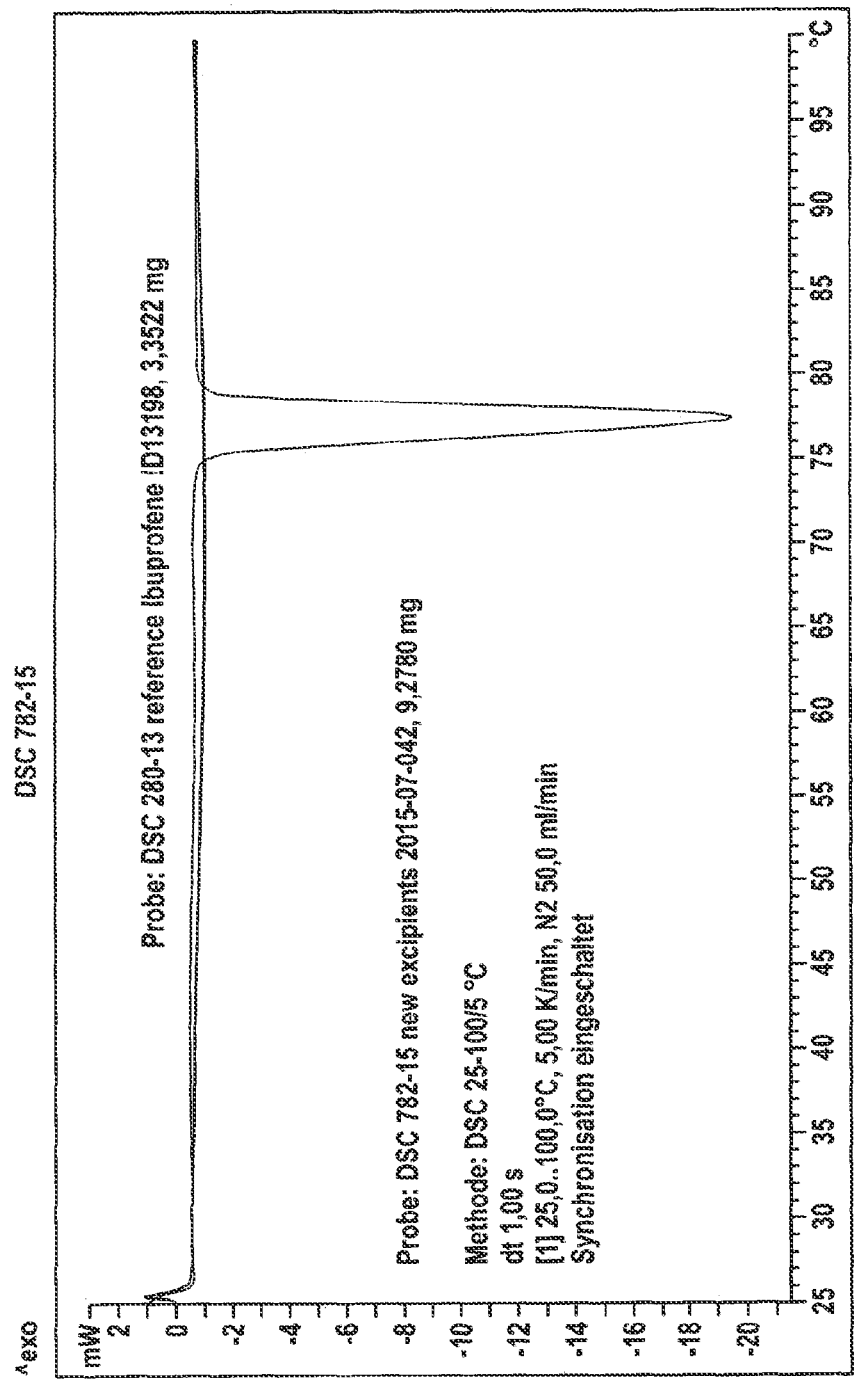
FIG. 7: DSC of an extruded composition comprising amorphous ibuprofen in a concentration of 40% w/w.
Figure 8:
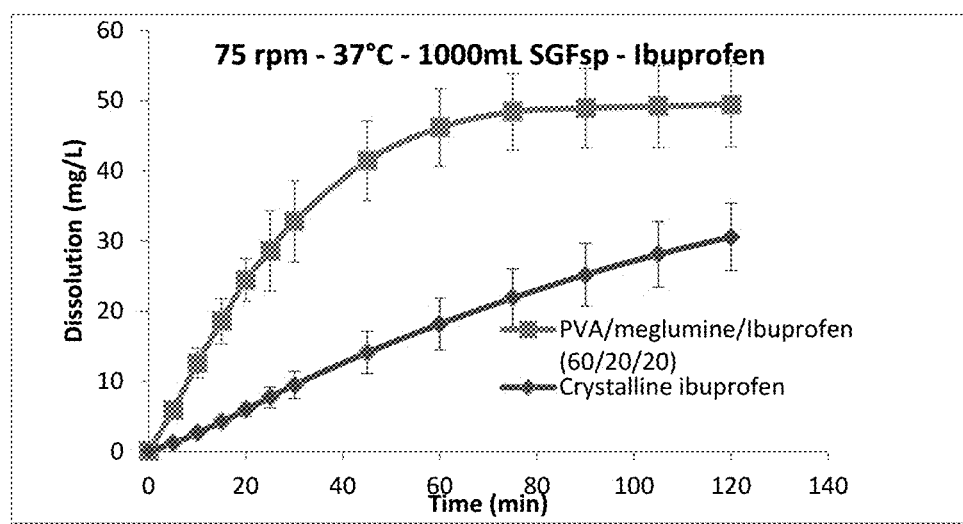
FIG. 8: Dissolution of 20% w/w ibuprofen loading in SGFsp medium at 37° C.

A: Extrusion process: the extrusion of ibuprofen (20-30%) and PVA 4-88 (70-80%) is not feasible, because the Tm of ibuprofen is too low (78° C.) for PVA4-88 (Tm=190° C.). In this case, the plasticizer is necessary to be added to reduce the Tg/Tm of PVA and make the extrusion process feasible. We added 25% meglumine as plasticizer and the mixture with meglumine is extrudable:
FIG. 4: Extrudate of 20% Ibuprofen with PVA/meglumine (75/25): 80° C./150° C./150° C./150° C./150° C.
B: Polymorphy of extrudated ibuprofen:
The polymorphy of extruded ibuprofen is evaluated, and extrudates comprising ibuprofen in concentration of 20% to 40% in amorphous form:
FIG. 5: DSC of an extruded composition comprising amorphous ibuprofen in a concentration of 20% w/w.
FIG. 6: DSC of an extruded composition comprising amorphous ibuprofen in a concentration of 30% w/w.
FIG. 7: DSC of an extruded composition comprising amorphous ibuprofen in a concentration of 40% w/w.
C: Dissolution of 20% w/w ibuprofen loading in SGFsp medium at 37° C.:
FIG. 8: Dissolution of 20% w/w ibuprofen loading in SGFsp medium at 37° C.

Example 2: Itraconazole

A: Extrusion process:
An extrusion temperature of 210° C. is necessary for the preparation of a physical mixture of PVA 4-88/itraconazole (70/30). With the addition of 17.5% meglumine as plasticizer, the extrusion temperature was reduced to 180° C.
B: Dissolution of itraconazole in SGFsp medium at 37° C.:
The dissolution of Itraconazole with meglumine is as well as without meglumine. But with the addition meglumine we can reduce the processing temperature very effectively.

Figure 9:
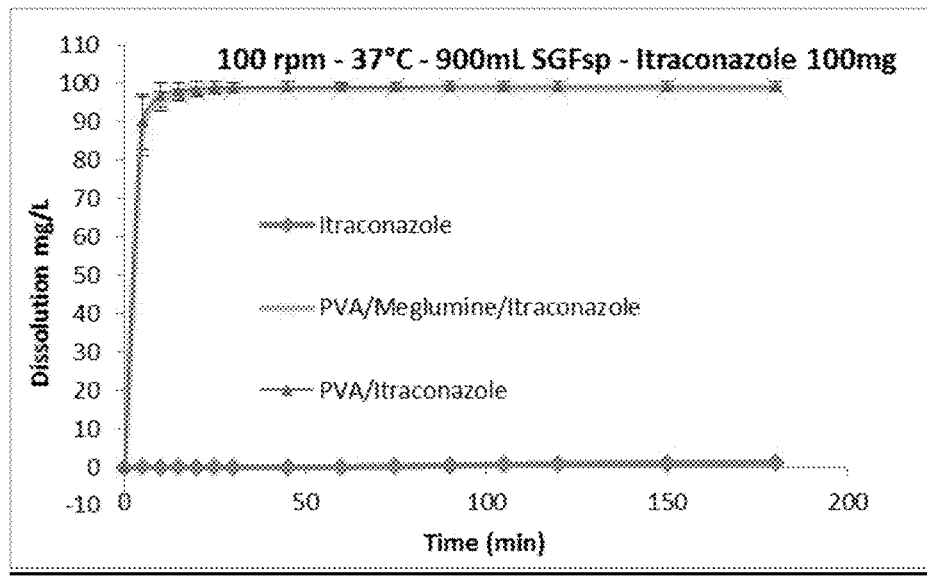
FIG. 9: Dissolution of 30% w/w itraconazole loading in SGFsp medium at 37° C.

FIG. 9: Dissolution of 30% w/w itraconazole loading in SGFsp medium at 37° C.

Example 3: Telmisartan

A: Extrusion process: an extrusion temperature of 240° C. is necessary for the physical mixture of PVA 4-88/telmisartan (85/15), because telmisartan has a high Tm of 261-263° C. With the addition of 21.25% meglumine as plasticizer in the mixture, the extrusion temperature could be reduced to from 240° C. to 180° C.

Figure 10:
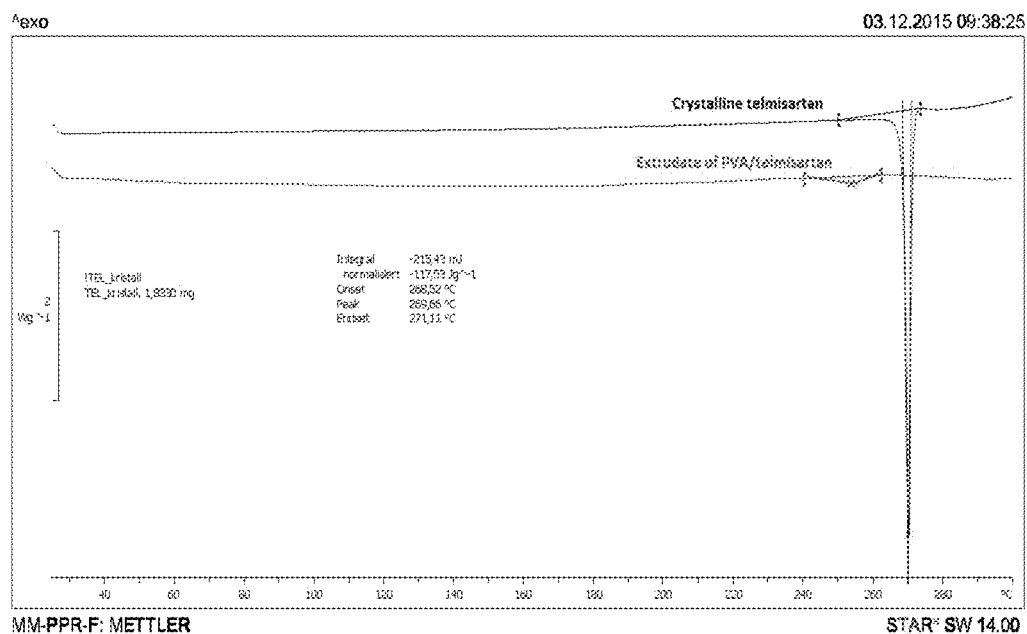
FIG. 10: DSC showed that extrudate from PVA/telmisartan is semi-crystalline.

B: Polymorphy of extrudated telmisartan: the DSC data showed us that the extrudate of 15% telmisartan within pure PVA4-88 is semi-crystalline, while the extrudate of PVA/meglumine/Telmisartan (63.75/21.25/15) is totally amorphous:

FIG. 10: DSC showed that extrudate from PVA/telmisartan is semi-crystalline

Figure 11:
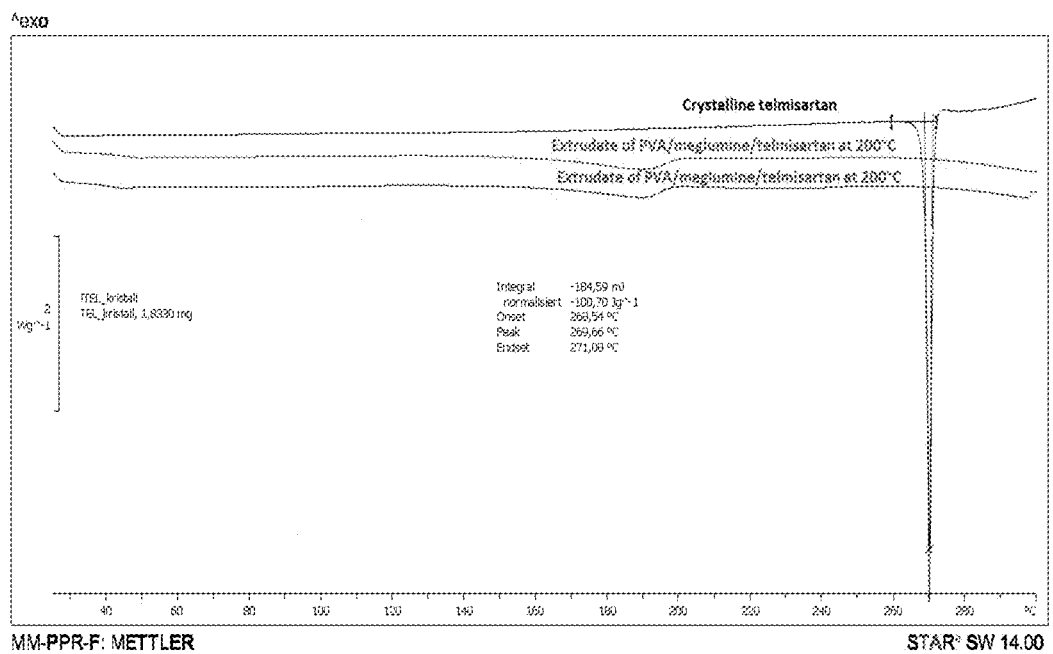
FIG. 11: DSC showed that extrudate from PVA/meglumine/telmisartan is 100% amorphous.

FIG. 11: DSC showed that extrudate from PVA/meglumine/telmisartan is 100% amorphous C: Dissolution of telmisartan in phosphate buffer pH 7.2 medium at 37° C.:

The dissolution of telmisartan could be improved effectively by addition of 21.25% meglumine, which is 5.6 fold higher than the dissolution without addition of meglumine. Therefore, in the case of telmisartan, meglumine is not only plasticizer, but it is also an effective solubility-enhancer, which improves the water solubility of active ingredients of BCS classes II and IV.

Figure 12:
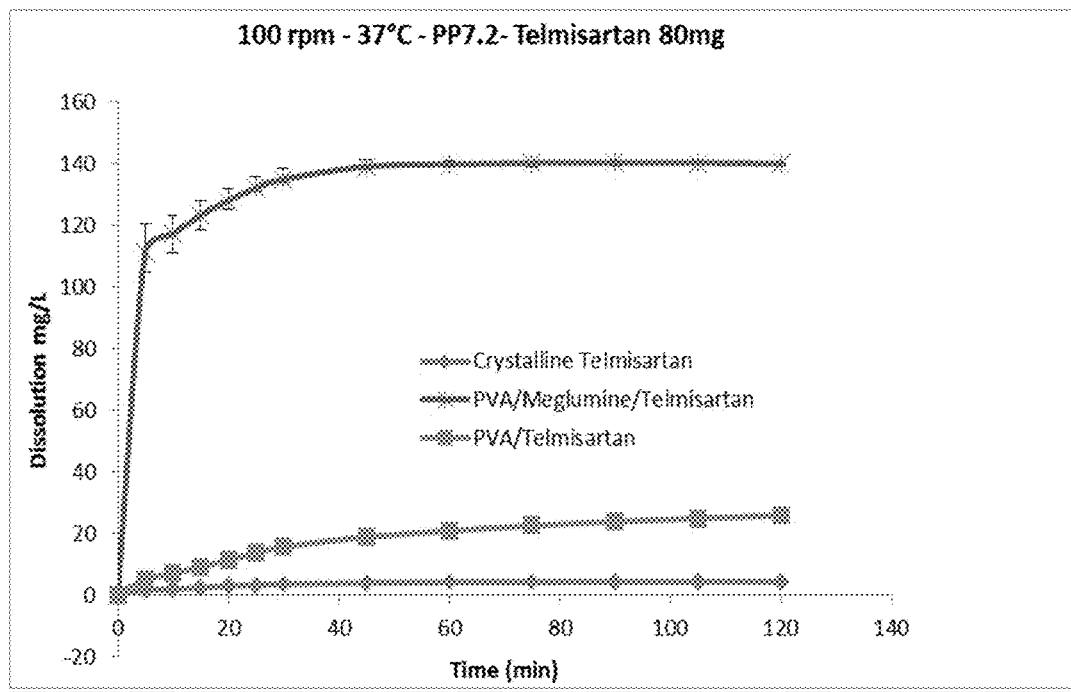
FIG. 12: Dissolution of telmisartan (15% w/w loading) in phosphate buffer pH 7.2 medium at 37° C.

FIG. 12: Dissolution of telmisartan (15% w/w loading) in phosphate buffer pH 7.2 medium at 37° C.

Example 4: Naproxen

A: Extrusion process: an extrusion temperature of 200° C. is necessary for the physical mixture of PVA 4-88/Naproxen (70/30), because Naproxen has a $T_m$ of 152° C. With the addition of 21.25% meglumine as plasticizer in the mixture, the extrusion temperature can be reduced from 200° C. to 160° C.

B: Dissolution of Naproxen in phosphate buffer pH 7.4 medium at 37° C.:

The dissolution of Naproxen can be improved effectively by addition of 21.25% meglumine, which is 1.26 fold higher than the dissolution without addition of meglumine. Therefore, in the case of Naproxen, meglumine is not only plasticizer, but it is also an effective solubility-enhancer, which improves the water solubility of active ingredients of BCS classes II and IV.

Figure 13:
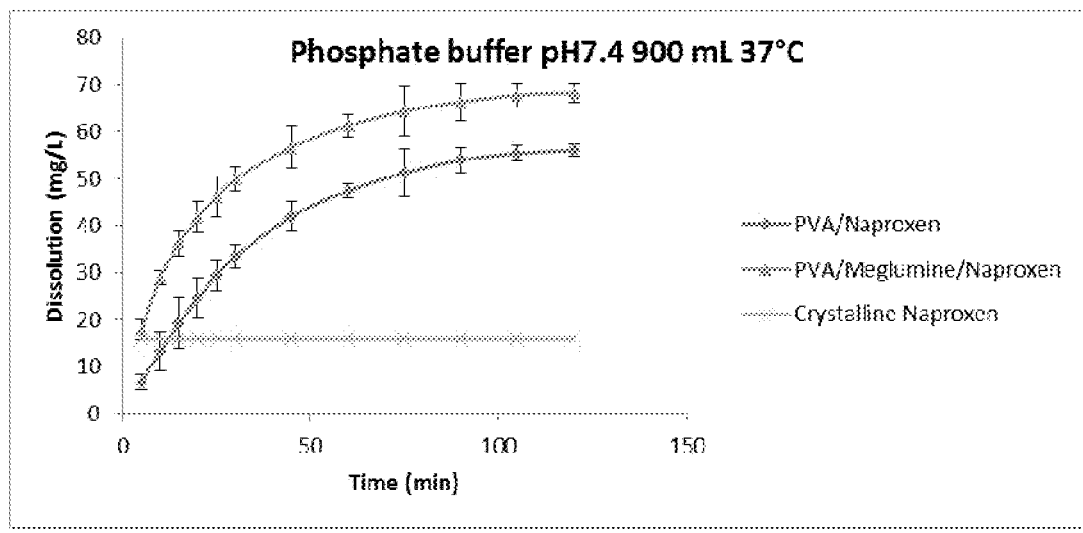
FIG. 13: Phosephate Buffer ph7.4 900 ml at 37° C.

FIG. 13: Dissolution of naproxen (30% w/w loading) in phosphate buffer pH 7.4 medium at 37° C.

4.1.2.3. Homogeneity of Active Ingredients within the Extruded Product

TABLE 2

Detected Ibuprofen concentration within extrudate (PVA/meglumine/ibuprofen = 60/20/20), which should contain 20% ibuprofen:

| Samples | Extrudate [mg] | Ibuprofen (HPLC method) [mg] | Ibuprofen loading [%] | Standard Deviation |
|---|---|---|---|---|
| 1 | 87.4 | 17.39 | 19.90 | 0.063 |
| 2 | 87.4 | 17.40 | 19.91 | |
| 3 | 97.5 | 19.25 | 19.75 | |
| 4 | 97.5 | 19.43 | 19.92 | |
| 5 | 91.13 | 18.09 | 19.86 | |
| 6 | 91.13 | 18.10 | 19.86 | |

TABLE 3

Detected itraconazole concentration within extrudate (PVA/meglumine/itraconazole = 52.5/17.5/30), which should contain 30% itraconazole

| Samples | Extrudate [mg] | Itraconazole (HPLC method) [mg] | Itraconazole loading [%] | Standard Standard Deviation |
|---|---|---|---|---|
| 1 | 84.01 | 25.23 | 30.01 | 0.297 |
| 2 | 86.89 | 25.93 | 29.84 | |
| 3 | 80.8 | 24.43 | 30.23 | |
| 4 | 91.38 | 27.20 | 29.77 | |
| 5 | 88.32 | 25.94 | 29.37 | |
| 6 | 88.65 | 26.33 | 29.70 | |

4.1.2.4. Increased Thermo-Stability of Active Ingredient

Ibuprofen is not extrudable with PVA alone because the $T_g$ of PVA is too high for ibuprofen. In this case a plasticizer is needed. The experiments show, that ibuprofen is extrudable at 150° C., if meglumine is added as plasticizer. Literature data show that 11.6% of the comprising Ibuprofen is degraded at 144° C., if the composition is processed by HME. In contrast, no degradation of Ibuprofen in presence of meglumine is observed (99% ibuprofen is detected in the final extrudate with ibuprofen as active ingredient). This means, that by the experiments it is found that in the case of ibuprofen meglumine not only acts as a plasticizer but it is also effective for stabilization against the negative influence of high temperatures. Thus meglumine acts in these compositions in the presence of ibuprofen as a heat stabilizer.

TABLE 4

Detected ibuprofen within extrudate comprising meglumine:

| Sample | Extrusion Temperature [° C.] | Ibuprofen after HME [%] |
|---|---|---|
| 1 | 150 | 99.51 |
| 2 | 150 | 99.53 |
| 3 | 150 | 98.73 |
| 4 | 150 | 99.62 |
| 5 | 150 | 99.28 |
| 6 | 150 | 99.31 |

TABLE 5

Detected ibuprofen within extrudate without meglumine (sorbitol as plasticizer):

| Sample | Extrusion Temperature [° C.] | Ibuprofen after HME [%] |
|---|---|---|
| 1 | 160 | 81.61 |
| 2 | 160 | 78.93 |
| 3 | 160 | 70.83 |
| 4 | 160 | 81.60 |

4.1.2.5 Summary of Results

The experiments clearly show that meglumine can be excellently used as plasticizers in drug-containing compositions, which contain as carrier PVA and which are processed by HME. In particular, these compositions exhibit the following advantageous properties:

- effectively reduced processing temperature during HME (samples with all 3 APIs)
- protection of thermo-sensitive APIs against thermo-degradation (sample with ibuprofen)
- improved water solubility of acidic active ingredients (samples with ibuprofen and telmisartan)
- no unexpected chemical interaction with active ingredients (samples with all 3 APIs)

What is claimed:

1. A process for plasticizing a polyvinyl alcohol (PVA) polymer containing composition comprising adding meglumine to the composition such that the composition comprises:
   0.5 to 40 weight percent of the meglumine relative to the total weight of the composition;
   60 to 95 weight percent of the PVA relative to the total weight of the composition; and
   0.1 to 40 weight percent of an active pharmaceutical ingredient (API) relative to the total weight of the composition;
wherein the meglumine reduces the melting temperature ($T_m$) and glass transition temperature ($T_g$) of the composition in a hot melt extrusion (HME) or melt extrusion process.

2. The process according to claim 1, wherein the meglumine reduces thermal degradation of the API during the HME or melt extrusion process if the API is thermosensitive.

3. The process according to claim 1, wherein the meglumine enhances water solubility of the API during the HME or melt extrusion process if the API is acidic.

4. A powdery composition, comprising:
   0.5 to 40 weight percent of meglumine relative to the total weight of the composition;
   60 to 95 weight percent of PVA relative to the total weight of the composition;
   0.1 to 40 weight percent of an API relative to the total weight of the composition; and
   optionally one or more additives selected from the group consisting of: a surface active material, anti-oxidant, stabilizing agent, solubility enhancing agent, pH control agent and flow regulator;
wherein the powdery composition is an amorphous solid dispersion of the API in a carrier matrix of the PVA, the meglumine, and the one or more additives.

5. A process for the production of a powdery composition according to claim 4, comprising:
   a) physically blending or granulating the PVA, the meglumine, the API and optionally the one or more additives into a homogeneous mixture;
   b) hot melt extruding or melt extruding the homogeneous mixture, thereby forming an amorphous solid dispersion of the API in a carrier matrix of the PVA, the meglumine, and optionally the one or more additives; and
   c) confectioning the amorphous dispersion into the powdery composition.

6. The process according to claim 5, wherein the hot melt extruding or melt extruding is performed at a temperature less than 150° C.

7. A process for the production of an amorphous composition comprising 0.5 to 40 weight percent of meglumine relative to the total weight of the composition; 60 to 95 weight percent of PVA relative to the total weight of the composition; 0.1 to 40 weight percent of an API relative to the total weight of the composition; and optionally one or more additives selected from the group consisting of: a surface active material, anti-oxidant, stabilizing agent, solubility enhancing agent, pH control agent and flow regulator, wherein the composition is an amorphous solid dispersion of the API in a carrier matrix of the PVA, the meglumine, and the one or more additives; the process comprising:
   a) physically blending or granulating the PVA, the meglumine, the API and optionally the one or more additives into a homogeneous mixture; and
   b) hot melt extruding or melt extruding the homogeneous mixture, thereby forming an amorphous solid dispersion of the API in a carrier matrix of the PVA, the meglumine, and optionally the one or more additives.

* * * * *